United States Patent [19]

Matsumori

[11] Patent Number: 5,545,623
[45] Date of Patent: Aug. 13, 1996

[54] METHOD OF INHIBITING SECRETION OF INFLAMMATORY CYTOKINES

[75] Inventor: Akira Matsumori, 16-22, Segawa 5-chome, Minoh-shi, Osaka, Japan

[73] Assignees: Akira Matsumori, Osaka; Otsuka Pharmaceutical Co., Ltd., Tokyo, both of Japan

[21] Appl. No.: 486,579

[22] Filed: Jun. 7, 1995

[30] Foreign Application Priority Data

Jun. 10, 1994 [JP] Japan ................................ 6-128765

[51] Int. Cl.$^6$ ................................ A61K 31/70
[52] U.S. Cl. ................................ 514/26; 536/5
[58] Field of Search ................................ 514/26; 536/5

[56] References Cited

U.S. PATENT DOCUMENTS 4,198,391  4/1980  Grainger ................................ 514/26

*Primary Examiner*—Elli Peselev
*Attorney, Agent, or Firm*—Sughrue, Mion, Zinn, Macpeak & Seas

[57] ABSTRACT

The present invention discloses a method of inhibiting secretion of inflammatory cytokines in a host which includes administering one or more digitalis compounds in an amount effective for inhibiting secretion of an inflammatory cytokine to the host in need of inhibition of secretion of the inflammatory cytokine. The invention also discloses a method of treating diseases caused by abnormal formation or abnormal secretion of inflammatory cytokines. The invention is useful in the treatment of various diseases ascribed to abnormal secretion/formation of IL=6, IL-8, MCAF, G-CSF and/or GM-CSF.

16 Claims, No Drawings

METHOD OF INHIBITING SECRETION OF INFLAMMATORY CYTOKINES

BACKGROUND OF THE INVENTION

1. Field of the Invention

The present invention relates to a method of inhibiting secretion of inflammatory cytokines in a host, and also to a method of treating diseases which involve abnormal production or abnormal secretion of inflammatory cytokines.

2. Description of the Related Art

A variety of inflammatory cytokines have been reported to be abnormally produced in many inflammatory diseases. As their participation in the mechanism of causing symptoms or pathology of the inflammatory diseases has gradually been clarified, clinical application of cytokines is now hoped for by controlling their production or developing antagonists thereto.

Differentiation of cells, in which B cells activated as a result of stimulation by antigens are proliferated into antibody-forming cells, requires the presence of certain cytokines. Among cytokines, interleukin-4 and interleukin-5 which correspond to BCGF (B cell growth factor) I and II are known to participate in proliferation of cells. Interleukin-6 (hereinafter referred to as IL-6) which is a B cell differentiation factor (BCDF) is a cytokine known to participate in differentiation.

IL-6 was first found in a supernatant of a peripheral blood monocyte culture as a factor which induces immunoglobulin production in strains of B cells transformed with EB viruses. Thereafter, they were separately investigated as independent factors such as B cell stimulatory factor-2 (BSF-2), interferon-β2 (IFN-β2), 26 kDa protein, hepatocyte stimulatory factor, and hybridoma plasmacytoma growth factor (HPGF) until cloning carried out by Hirano et al. in 1986 revealed that all of them are identical cytokines [Hirano, T. et al., Nature, 324, 73 (1986)].

It has been clarified that IL-6, which has important functions in the antibody-forming system of B cells in the immune system, also serves as an important factor in the protective system of living bodies such as the hematopoietic system, the nervous system, and liver, by inducing proliferation and differentiation of T cells, acting on liver cells to stimulate synthesis of acute proteins, or by stimulating the hematopoietic cells to form pluripotent colonies.

Present knowledge and reports on IL-6 or the relationship between abnormal formation or secretion of IL-6 and various diseases are as follows.

In autoimmune diseases such as hypergamma-globulinemia, rheumatoid arthritis (RA) which shows positive results against various autoantibodies, and systemic lupus erythematosus (SLE), activation of polyclonal B cells is induced. In a synovial fluid of RA patients, a great amount of IL-6, which is formed by activated T cells or B cells infiltrated into the synovial membrane tissue, is present [Hirano, T. et al., Eur. J. Immunol., 18, 1797 (1988)].

It is reported that in patients suffering from atrial myxoma and presenting symptoms of autoimmune diseases, the clinical symptoms disappear after tumors are removed. This suggests that some factor produced by tumor cells induces the symptoms. It has also been shown that tumor cells produce a great deal of IL-6, suggesting a connection between abnormal formation of IL-6 and a disease with abnormality in polyclonal B cells [Hirano, T. et al., Proc. Natl. Acad. Sci., USA, 82, 5490 (1985)].

IL-6 had already been reported to be a growth factor of mouse plasma cytoma. Recently, based on the fact that proliferation of myeloma cells obtained from human multiple myelomatosis patients is suppressed by anti-IL-6 antibodies, it has now been considered that IL-6 has the possibility of being an autoproliferation factor of myeloma cells. This suggests that IL-6 greatly participates not only in polyclonal B cell abnormalities but also in monoclonal B cell abnormalities such as myeloma [Kawano, M., et al., Nature, 332, 83 (1988)].

In Castleman syndrome accompanied by noncausal lymph node enlargement, high blood IL-6 activity is observed as well as hypergamma-globulinemia and high levels of acute proteins. When swollen lymph nodes are removed from the patients, blood IL-6 activity returns to a normal serum level, and the patients' clinical conditions are ameliorated [Yoshizaki, K. et al., Blood, 74, 1360 (1989)].

In urine samples from patients with primary glomerulonephritis, significant IL-6 activities are observed compared to samples of healthy subjects or patients with minimal change nephrotic syndrome. In tissue samples of kidney biopsy, the degree of proliferation of mesangium cells and urinary IL-6 activity are correlated. In fact, when IL-6 is added to an in vivo culture system of rat renal mesangium cells, proliferation of the cells is stimulated in a concentration dependent manner. This proves that IL-6 is a proliferative factor of mesangium cells [Horii, Y. et al., J. Immunol. 143, 3949 (1989)].

Interleukin-8 (IL-8) is a potent chemotactic and activating cytokine for neutrophilic leukocytes. It is considered to participate in various inflammatory diseases, and its clinical application is expected to be developed by controlling their formation or developing antagonists thereto. A number of reports have already been published which deal with abnormal formation of IL-8 and inflammatory diseases associated therewith. Presently, research of clinical application using anti-IL-8 antibodies is conducted [Clinical Immunology, 27 (Suppl. 16), 80–85 (1995), among others].

A monocyte chemotactic and activating factor (MCAF) which is sometimes called MCP-1 (monocyte chemoattractant protein-1) has a structure and functions similar to those of the above-mentioned IL-8. In this regard, MCAF and IL-8 constitute a family. MCAF has monocyte-specific migrating activities and exhibits eosinocyte histamine releasing actions, and therefore, it is considered to be greatly involved in inflammation and bioprotective mechanisms. Especially, its chemotactic and activating features on monocytes suggest that MCAF has some relation to inflammatory diseases, autoimmune diseases, arteriosclerosis, and tumors. On the other hand, its basophil activating feature suggests some relation to allergy reactions. In fact, it has now been clarified that overproduction of MCAF actually occurs to cause infiltration and activation of macrophages, resulting in a contribution in the formation of pathological conditions [Clinical Immunology, 27 (Suppl. 16), 155–161 (1995), among others].

A granolocyte-macrophage colony-stimulating factor (GM-CSF) has a variety of bioactivities not to speak of its outstanding role in the granulocyte/macrophage hematopoietic system. For example, like the above-mentioned cytokines, it is known to stimulate the functions of matured blood cells such as neutrophilic leukocytes, eosinocytes, and basophils. Abnormal formation of GM-CSF has been reported, for example, in RA patients, suggesting participation in the mechanism of the onset of arthritis. Moreover, from the fact that GM-CSF stimulates proliferation of white blood cells, the possibility of the presence of an autocrine growth mechanism is suggested to explain the infinite proliferation of the cells [Clinical Immunology, 27 (Suppl. 16), 202–211 (1995), among others].

Likewise, a granulocyte colony-stimulating factor (G-CSF) is known to stimulate the functions of mature neutrophilic leukocytes. It also stimulates proliferation of myeloid leukemia cells and part of solid cancerous cells [Clinical Immunology, 27 (Suppl. 16), 212–219 (1995), among others].

As mentioned above, a great many diseases are ascribed to abnormal formation or abnormal secretion of inflammatory cytokines. It is therefore considered that if secretion of inflammatory cytokines in a host typified by a human is successfully inhibited, it will be of help to the treatment of the host suffering from those diseases.

In view of the foregoing, the present inventors conducted research over various chemicals in search of substances which inhibit secretion of inflammatory cytokines, during which they unexpectedly found that digitalis compounds inhibit secretion of the inflammatory cytokines, leading to completion of the invention.

SUMMARY OF THE INVENTION

Accordingly, an object of the present invention is to provide a drug which is capable of curing a host with abnormal formation or abnormal secretion of inflammatory cytokines by inhibiting the secretion of inflammatory cytokines.

In one aspect of the present invention, there is provided a method of inhibiting secretion of inflammatory cytokines in a host which comprises administering one or more digitalis compounds in an amount effective for inhibiting secretion of an inflammatory cytokine to the host in need of inhibition of secretion of the inflammatory cytokine.

In another aspect of the present invention, there is provided a method of treating a disease associated with abnormal formation or secretion of inflammatory cytokines which comprises administering one or more digitalis compounds in an amount effective for inhibiting secretion of an inflammatory cytokine to the host with abnormal formation or secretion of inflammatory cytokines.

The above and other objects, features, and advantages of the present invention will become apparent from the reading of the following description.

DETAILED DESCRIPTION OF THE INVENTION AND PREFERRED EMBODIMENTS

Digitalis compounds have $Na^+$-$K^+$-ATPase activity inhibiting actions, and are widely used as a cardiac tonic when catecholamine agents are withdrawn or in the treatment of mild cardiac failures in outpatient services. They are also known to be effective in inhibiting cardiac rate and preventing atrial fibrillation and paroxysmal supraventricular tachycardia of patients with atrial fibrillation. The compounds exhibit electrophysiological actions such as negative chronotropic action, atrioventricular conduction inhibitory action, and arrhythmia inducing action through the change in sensitivity of autonomic nerve receptors of cardiovascular systems or by an immediate action to the central nervous system. Moreover, digitalis intoxication including gastroenteric disorders is considered to be resulted through the action on the central nervous system. In addition, ouabain, a typical digitalis compound, is known to inhibit differentiation of lymphocytes and formation of IL-2 [Dornand, J., et al., Immunobiology, 171, 636 (1986) among others] as well as to inhibit anti-virus activities of interferons [Lebon, P., et al., Proc. Soc. Exptl. Biol. Med., 149, 108 (1975)].

However, the inflammatory cytokine secretoinhibitory actions of the digitalis compounds on which the present invention is founded are not only irrelevant to the above-mentioned pharmacological actions such as cardiotonic actions which are already known but also difficult to predict from those known actions.

The digitalis compounds which are used in the present invention as effective components are digitalis drugs which are conventionally used as cardiotonics for primarily treating cardiac failures. Examples of such digitalis compounds include ouabain (g-strophanthin), digitoxin, digoxin, β-methyldigoxin (β-MD), deslanoside, and lanatoside C, proscillaridin (nonproprietary names). Drugs containing these digitalis compounds are available from the market under trademarks of various pharmaceutical companies. In the present invention, such commercial products may also be used. For example, Uabanin (trademark, Takeda Pharmaceutical) may be used as ouabain. Among the abovementioned digitalis compounds, ouabain is also called g-strophanthin. It is a cardiac glycoside obtained from seeds of a plant *Strophantus gratus* or from the bark of *Acocanthera ouabaio*. It increases the level of heart contraction and inhibits conduction more potently than any other digitalis compounds. Accordingly, ouabain is a preferable compound which is used as the effective component in the method of the present invention.

In the present invention, the term inflammatory cytokine(s) is used to encompass IL-6, IL-8, MCAF, G-CSF, and GM-CSF. Therefore, the method of the present invention can cure diseases caused by abnormal formation or abnormal secretion of these cytokines.

Examples of the diseases caused by abnormal formation or abnormal secretion of IL-6 include cancerous cachexia, atrial myxoma, rheumatoid arthritis, autoimmune diseases, Castleman disease, myeloma, Lennert's lymphoma, mesangium proliferative nephritis, psoriasis, Kaposi's sarcoma associated with AIDS, and postmenopausal osteoporosis.

Examples of the diseases caused by abnormal formation or abnormal secretion of IL-8 include rheumatic and gouty arthritis including rheumatoid arthritis, psoriasis, adult respiratory distress syndrome, asthma, immunoangiitis, sepsis, ischemic diseases such as myocardial infarct and multiple organ failure, viral and alcoholic hepatitis, bacterial and viral meningitis, Crohn's disease, pyelonephritis, uveitis, and Mediterranean fever.

Examples of the diseases caused by abnormal formation or abnormal secretion of MCAF include infectious diseases, rheumatoid arthritis, arteriosclerosis, arterial stenosis after angioplasty, glomerulonephritis, and malignant tumors.

Examples of the diseases caused by abnormal formation or abnormal secretion of G-CSF include diseases caused by hyperenergia of neutrophilic leukocytes and malignant tumors.

Examples of the diseases caused by abnormal formation or abnormal secretion of GM-CSF include rheumatoid arthritis and malignant tumors.

In the method of the present invention, the active components, i.e., the digitalis compounds, may be prepared into a variety of forms depending on the kind of the compound and used. The forms and administration routes may be the same as those employed in the use of commercial digitalis compounds. For example, in use of ouabain agents, they are usually prepared into injections, for ouabain is easily decomposed in gastrointestinal tracts or its intestinal absorption rate is low. When they are prepared into injections, the liquid media, suspending agents, and the like are preferably sterilized and isotonic with blood. In the manufacture of liquid agents, emulsions, and suspensions, any diluent commonly employed in this technical field can be used. For example, water, alcohols, propylene glycols, ethoxylated isostearyl alcohols, polyoxyethylene isostearyl alcohols, and polyoxyethylene sorbitan fatty acid esters can be used as the diluent. NaCl, glucose, or glycerol may also be incorporated in the injection preparations in amounts sufficient to prepare isotonic solutions. Moreover, ordinary solution adjuvants, buffers, and analgesic agents may also be added.

The dose of the above-mentioned pharmaceutical agents varies depending on the manner of administration, age, sex, and other conditions of the patient, severity of the disease, etc. Usually, the amount of the effective component, i.e., digitalis, is about 0.01 to 1.0 mg/day. The amount of the effective component in the unit physical form of administration is preferably from about 0.005 to 0.5 mg.

As described above, according to the present invention, a method of inhibiting secretion of inflammatory cytokines is provided, in which a digitalis compound, in particular, ouabain which is a type of cardiotonic glycosides, is used as an effective agent. The method of the invention is capable of effectively curing the aforementioned various diseases caused by abnormal secretion/formation of IL-6, IL-8, MCAF, G-CSF and/or GM-CSF.

EXAMPLES

The present invention will described in more detail by way of examples which include preparatory examples and pharmacological test examples.

Human umbilical vein endothelial cells (HUVEC) were isolated using a modified method of Gimbrone et al. [Gimbrone M. A., et al., J. Cell Biol., 60, 673–684 (1974)], and cultured using a medium of Medium 199 (Sigma) with 20% fetal calf serum (FCS), 30 µg/ml of endothelial cell growth supplement (ECGS) (Sigma), and 90 µg/ml of heparin (Sigma). Briefly, umbilical veins were cannulated, filled with a solution of 0.05% collagenase (Worthington Biochemical Corporation, USA), and incubated for 20 minutes at 37° C. The contents were emptied into conical tubes containing the medium and then centrifuged. The pellet cells were seeded and cultured on tissue culture plastic precoated with gelatin and maintained in a tissue culture incubator at 37° C. in a 5% $CO_2$ atmosphere. The HUVEC used in this study were comprised of passage levels 3 to 5.

The HUVEC were placed in 24-well plates ($2 \times 10^5$ cell/ml medium). To each well, a predetermined amount (M) of ouabain (product of Wako Junyaku) was added, after which 10 ng/ml of interleukin-1β (Genzyme, USA) was added to stimulate the cells under incubation at 37° C. for 24 hours. The supernatant obtained after centrifugal separation was subjected to measurement of inflammatory cytokines by ELISA using a plate with antibodies to the cytokines immobilized thereon. The assay was carried out using commercial kits (Otsuka Pharmaceutical and Toray Fuji Bionics) or in a substantially identical manner (the same applies to the following tests).

The results are shown in Table 1 together with the ouabain concentrations (M) used. In Table 1, the results of samples which did not contain ouabain are shown as controls, and relative values (%) based on the control values (=100%) are also shown.

As is apparent from Table 1, addition of ouabain inhibits secretion of inflammatory cytokines dose-dependently.

TABLE 1

| Cytokines | | Amounts of ouabain added (M) | | | |
|---|---|---|---|---|---|
| | | 0 (Control) | $10^{-8}$ | $10^{-7}$ | $10^{-6}$ |
| IL-6 | Concentration (pg/ml) | 579.3 ± 49.2 | 567.3 ± 84.6 | 230.7 ± 21.2 | 108.0 ± 11.4 |
| | Relative value (%) | 100 | 99.0 ± 22.2 | 40.2 ± 7.4 | 18.8 ± 2.9 |
| G-CSF | Concentration (pg/ml) | 9016.7 ± 667.1 | 8956.7 ± 1223.5 | 2143.3 ± 118.5 | 1430.0 ± 194.7 |
| | Relative value (%) | 100 | 100.0 ± 17.9 | 23.9 ± 3.2 | 16.0 ± 3.2 |
| GM-CSF | Concentration (pg/ml) | 564.7 ± 38.8 | 603.0 ± 94.8 | 530.3 ± 37.7 | 220.3 ± 21.1 |
| | Relative value (%) | 100 | 110.3 ± 26.2 | 94.5 ± 13.3 | 39.3 ± 5.8 |
| IL-8 | Concentration (pg/ml) | 47.0 ± 2.5 | 46.2 ± 4.9 | 28.5 ± 1.6 | 15.2 ± 0.8 |
| | Relative value (%) | 100 | 98.7 ± 14.6 | 60.6 ± 0.3 | 32.4 ± 3.1 |
| MCAF | Concentration (pg/ml) | 30.8 ± 1.7 | 30.0 ± 3.0 | 19.4 ± 1.0 | 4.8 ± 0.7 |
| | Relative value (%) | 100 | 98.2 ± 15.0 | 63.1 ± 2.2 | 15.6 ± 2.2 |

(n = 3, mean ± SD)

Example 1

Effects on cytokine formation in human umbilical vein endothelial cells (HUVEC):

Example 2

Effects on cytokine formation in peripheral blood monocytes:

Monocytes were separated from peripheral blood samples of healthy humans using a Ficoll-paque solution (Pharmacia), and washed three times with PBS (phosphate buffered saline). Subsequently, the monocytes were cultured in a 24-well plate using an RPMI 1640 culture broth (Gibco) containing 10% thermally inactivated FCS (Gibco)($2\times10^6$ cells/ml). After a predetermined amount (M) of ouabain was added thereto, the monocytes were stimulated by the addition of (1) 1 μg/ml of LPS (lipopolysaccharide; Difco) or (2) 1 μM of ionomycin (Calbiochem) and 1 ng/ml of PMA (Sigma). Twenty hours later, the mixture was centrifugally separated (1,200 rpm, 15 min.) to determine the amount of inflammatory cytokines in the supernatant by ELISA.

Similar to Table 1, the results obtained in stimulations (1) and (2) are shown in Tables 2 and 3, respectively.

From the results, it is clear that ouabain inhibits inflammatory cytokine secretion stimulated by LPS or ionomycin+PMA dose-dependently.

To 5 ml of an RPMI 1640 culture broth, 1 μg/ml of LPS and a predetermined amount of ouabain were added in this order. Thereafter, 5 ml of whole blood of a healthy human to which heparin (20 μ/ml, Shimizu Seiyaku) had been added was added thereto, and incubated at 37° C. for 24 hours. After centrifugal separation (1,500 rpm, 15 min.), the supernatant was subjected to measurement of the amount of IL-6 by ELISA.

The results are shown in Table 4.

As is apparent from Table 4, the addition of ouabain inhibits secretion of inflammatory cytokines.

TABLE 2

| Cytokines | | Amounts of ouabain added (M) | | | | | |
|---|---|---|---|---|---|---|---|
| | | 0 (Control) | $10^{-9}$ | $10^{-8}$ | $10^{-7}$ | $10^{-6}$ | $10^{-5}$ |
| IL-6 | Concentration (pg/ml) | 3969 ± 918 | 4038 ± 1134 | 3608 ± 800 | 2347 ± 809 | 758 ± 444 | 589 ± 413 |
| | Relative value (%) | 100 | 101 ± 10 | 92 ± 10 | 60 ± 17 | 19 ± 10 | 15 ± 9 |
| IL-8 | Concentration (pg/ml) | 28.3 ± 8.0 | — | 33.7 ± 11.1 | 15.3 ± 1.1 | 6.4 ± 0.1 | — |
| | Relative value (%) | 100 | — | 119.1 ± 20.4 | 57.7 ± 16.3 | 24.1 ± 6.9 | — |
| MCAF | Concentration (pg/ml) | 140.2 ± 94.7 | — | 110.7 ± 89.3 | 57.8 ± 50.8 | 14.8 ± 10.8 | — |
| | Relative value (%) | 100 | — | 83.1 ± 29.1 | 49.7 ± 28.2 | 11.6 ± 5.0 | — |

(n = 8, mean ± SD)

TABLE 3

| Cytokines | | Amounts of ouabain added (M) | | | | | |
|---|---|---|---|---|---|---|---|
| | | 0 (Control) | $10^{-9}$ | $10^{-8}$ | $10^{-7}$ | $10^{-6}$ | $10^{-5}$ |
| IL-6 | Concentration (pg/ml) | 1378 ± 945 | 1521 ± 1120 | 1445 ± 768 | 90 ± 78 | 20 ± 1 | <20 |
| | Relative value (%) | 100 | 111 ± 43 | 121 ± 42 | 6.7 ± 4.4 | 2.2 ± 1.4 | 2.2 ± 1.4 |

(n = 8, mean ± SD)

Example 3

Effects on cytokine production caused by whole blood stimulation by LPS:

TABLE 4

| Cytokines | | Amounts of ouabain added (M) | | | | | |
|---|---|---|---|---|---|---|---|
| | | 0 (Control) | $10^{-8}$ | $10^{-7}$ | $10^{-6}$ | $10^{-5}$ | $10^{-4}$ |
| IL-6 | Concentration (pg/ml) | 141 ± 67 | 130 ± 86 | 63 ± 42 | <20 | <20 | <20 |
| | Relative value (%) | 100 | 86 ± 36 | 42 ± 10 | <17 | <17 | <17 |

(n = 5, mean ± SD)

The whole content of the basic Japanese patent application No. 6-128,765 from which priority is claimed is incorporated herein by reference.

What is claimed is:

1. A method of inhibiting secretion of inflammatory cytokines in a host which comprises administering one or more digitalis compounds in an amount effective for inhibiting secretion of an inflammatory cytokine in the host in need of inhibition of secretion of the inflammatory cytokine.

2. The method according to claim 1, wherein the inflammatory cytokine is IL-6.

3. The method according to claim 1, wherein the inflammatory cytokine is IL-8.

4. The method according to claim 1, wherein the inflammatory cytokine is MCAF.

5. The method according to claim 1, wherein the inflammatory cytokine is G-CSF.

6. The method according to claim 1, wherein the inflammatory cytokine is GM-CSF.

7. The method according to claim 1, wherein the one or more digitals compounds are selected from the group consisting of ouabain, digoxin, digitoxin, β-methyldigoxin, deslanoside, lanatoside C, and proscillaridin.

8. A method of treating a disease associated with secretion of inflammatory cytokines in a host which comprises administering one or more digitalis compounds in an amount effective for inhibiting secretion of an inflammatory cytokine in the host suffering from a disease associated with secretion of inflammatory cytokines.

9. The method according to claim 8, wherein the inflammatory cytokine is IL-6.

10. The method according to claim 8, wherein the inflammatory cytokine is IL-8.

11. The method according to claim 8, wherein the inflammatory cytokine is MCAF.

12. The method according to claim 8, wherein the inflammatory cytokine is G-CSF.

13. The method according to claim 8, wherein the inflammatory cytokine is GM-CSF.

14. The method according to claim 8, wherein the one or more digitals compounds are selected from the group consisting of ouabain, digoxin, digitoxin, β-methyldigoxin, deslanoside, lanatoside C, and proscillaridin.

15. The method according to claim 1, wherein the one or more digitalis compounds are administered in a total amount ranging from 0.01 to 1.0 mg/day.

16. The method according to claim 8, wherein the one or more digitalis compounds are administered in a total amount ranging from 0.01 to 1.0 mg/day.

* * * * *